United States Patent [19]

Knott et al.

[11] 4,038,156

[45] July 26, 1977

[54] BUTADIENE RECOVERY PROCESS

[75] Inventors: Robert F. Knott; Arthur E. Handlos, both of Houston, Tex.

[73] Assignee: Shell Oil Company, Houston, Tex.

[21] Appl. No.: 725,065

[22] Filed: Sept. 21, 1976

[51] Int. Cl.² .......................... B01D 3/40; C07C 7/08
[52] U.S. Cl. ......................................... 203/45; 203/46; 203/60; 203/75; 203/77; 203/80; 203/88; 260/681.5 R
[58] Field of Search ................................... 203/43–46, 203/42, 60, 78, 75, 74, 77, 88, 80, 82; 260/681.5 R

[56] References Cited

U.S. PATENT DOCUMENTS

| | | | |
|---|---|---|---|
| 2,376,425 | 5/1945 | Frey | 260/681.5 R |
| 2,459,410 | 1/1949 | Brandon | 203/45 |
| 2,920,113 | 1/1960 | Pollack et al. | 260/681.5 R |
| 2,993,841 | 7/1961 | Sarno | 260/681.5 R |
| 3,436,436 | 4/1969 | Takao et al. | 260/681.5 R |
| 3,436,438 | 4/1969 | Takao et al. | 260/681.5 R |
| 3,772,158 | 11/1973 | Sarno | 203/60 |
| 3,798,132 | 3/1974 | Sarno | 203/60 |
| 3,844,902 | 10/1974 | Vickers et al. | 203/46 |

*Primary Examiner*—Wilbur L. Bascomb, Jr.

[57] ABSTRACT

An improvement is described on a process for recovery of butadiene from a C₄ hydrocarbon mixture additionally containing minor amounts of C₅ saturated and unsaturated hydrocarbons, said hydrocarbon mixture being obtained as the overhead product of an initial hydrocarbon fractionation employed to separate larger quantities of C₅ and heavier hydrocarbons from the hydrocarbon mixture, wherein the hydrocarbon mixture is subject to extractive distillation in the presence of a polar solvent e.g. acetonitrile, in which butadiene is separated from the fat solvent bottoms of extractive distillation by sequential low pressure flashing and stripping, followed by compression of the combined vapors of flashing and stripping with part of the compressed vapors being recycled as reboiled vapor to the extractive distillation and the remainder being again stripped at a higher pressure to recover butadiene therefrom. In this improved process, butadiene purification problems associated with carry over of C₅ hydrocarbons into the fat solvent bottoms of extractive distillation are avoided by condensing a portion of the combined and compressed vapor stream from low pressure flashing and stripping to obtain a condensed liquid stream relatively rich in C₅ hydrocarbons, which additionally contains butadiene and a small amount of polar solvent, followed by water washing of the condensed liquid stream to remove polar solvent therefrom and subsequent passing of the water-washed stream, substantially free of polar solvent, to the initial hydrocarbon fractionation employed to separate larger quantities of C₅ and heavier hydrocarbons, whereby C₅ hydrocarbons contained in the condensed liquid stream are substantially removed from the hydrocarbon mixture passed to extractive distillation.

8 Claims, 1 Drawing Figure

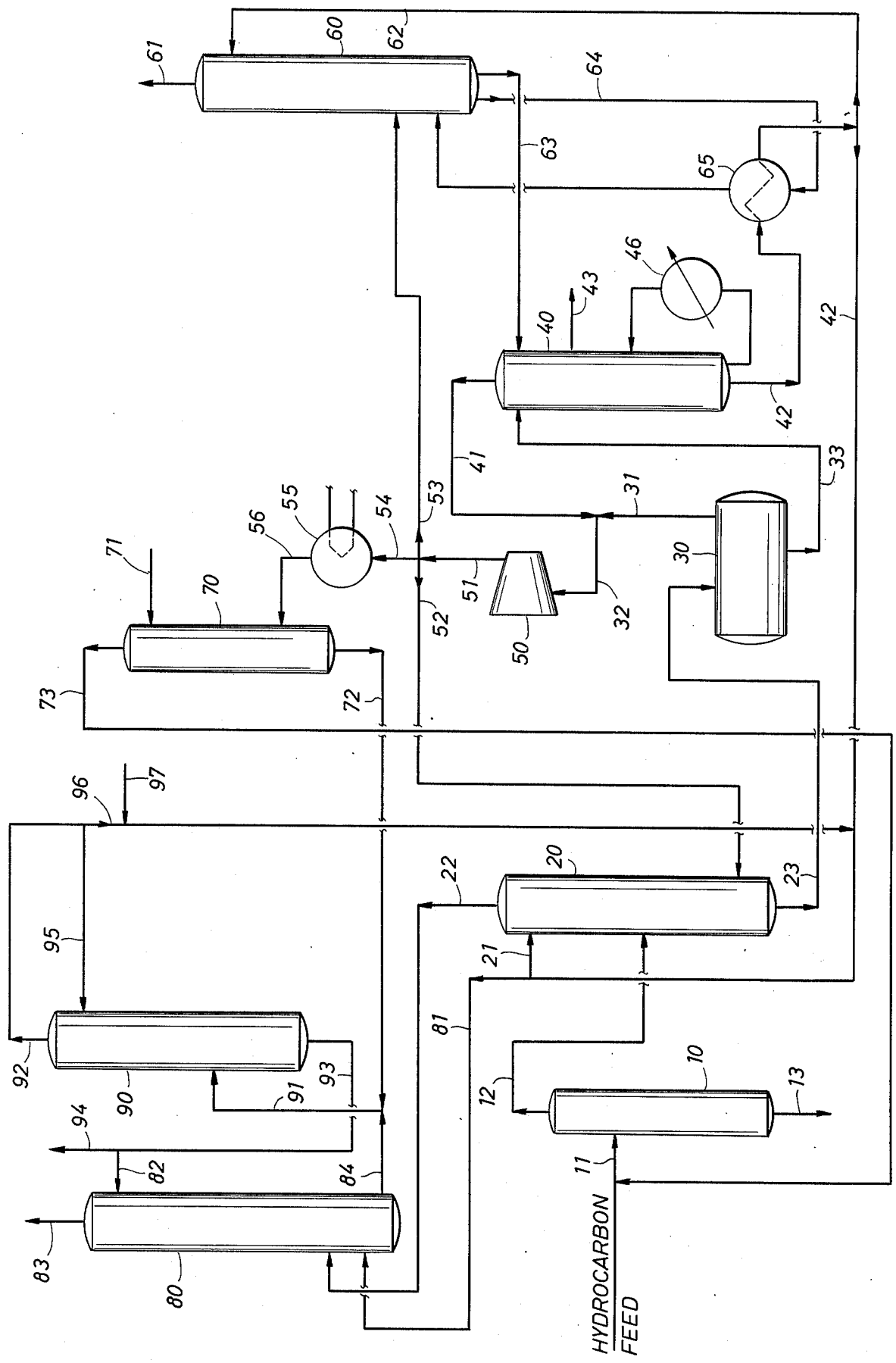

BUTADIENE RECOVERY PROCESS

BACKGROUND OF THE INVENTION

This invention relates to an improved extractive distillation process for separation and recovery of butadiene from mixtures of close boiling hydrocarbons. More particularly, this invention is directed to an improvement on the extractive distillation process described in U.S. Pat. No. 3,772,158, which avoids the problems associated with the buildup of $C_5$ hydrocarbons in the solvent phase of extractive distillation when said extractive distillation process is employed subsequent to conventional fractionation to recover butadiene from a $C_4$ hydrocarbon stream containing minor amounts of $C_5$ saturated and unsaturated hydrocarbons.

Conventional processes for the production of butadiene, an important starting material in the manufacture of synthetic rubbers, pharmaceuticals and the like, invariably include a process step or sequence of process steps wherein butadiene must be separated and recovered from a mixture of hydrocarbon components whose normal volatities are such that separation cannot readily be achieved by ordinary fractional distillation. In these conventional processes, the source of butadiene is typically a non-selective dehydrogenation of pyrolysis operation which yields butadiene in admixture with a variety of other saturated and unsaturated hydrocarbons including compounds of like carbon number and different degrees of unsaturation which are very difficult to separate one from another. According to industry practice, butadiene is suitably recovered and purified in these instances through the application of an extractive distillation technique which alters the relative volatilities of the hydrocarbon components in the mixture and thereby makes the separation by distillation possible. In a typical extractive distillation procedure, the distillation of the butadiene-containing hydrocarbon mixture is carried out in the presence of a polar solvent such as acetonitrile, acetone, furfural, dimethylformamide and their corresponding aqueous mixtures, which enhances the volatility of the less unsaturated components relative to the more unsaturated compounds. In such an extractive distillation process, compounds such as butanes and butenes exhibit higher volatilities and are recovered as overhead product whereas diolefins such as butadiene and higher acetylenes, being less volatile, are separated together with the polar solvent as the fat solvent, bottoms product from the extractive distillation zone. Depending on the extractive distillation process selected, the butadienecontaining fat solvent is then passed to one or more flashing and/or stripping zones operated at elevated temperatures and/or reduced pressure for separation and recovery of the purified butadiene.

One conventional extractive distillation process which is eminently suitable for the recovery of butadiene from mixtures of close boiling hydrocarbons, including butanes and butenes, is that described in U.S. Pat. No. 3,772,158 to Sarno. In this process, conventional extractive distillation is carried out in the presence of a polar solvent e.g. acetonitrile, and butadiene is initially recovered from the fat solvent bottoms product at low pressure as a butadiene-rich vapor by sequential flashing and stripping of the unflashed liquid product in a flash zone and a first stripping zone operated at pressures lower than that of the extractive distillation zone. The butadiene-rich, vapor products of low pressure flashing and stripping are then combined and compressed to a pressure higher than of the extractive distillation zone and a portion of this compressed vapor is recycled to the bottom of the extractive distillation zone with the remainder of the vapor being passed to a second stripping zone wherein butadiene is recovered as an overhead product. The process described in the Sarno patent is especially advantageous in providing for comparatively low temperatures in the flashing and stripping zones of the process, thus minimizing or avoiding polymerization of diolefins and acetylenes, while at the same time reducing the heat energy, refrigeration and compression requirements of the system.

While this patented process has found substantial commercial acceptance, there are situations in which its application is less than optimum. One such situation where problems arise is when the hydrocarbon feedstock to extractive distillation contains minor but significant amounts of $C_5$ saturated and/or unsaturated hydrocarbons. This situation typically occurs in the recovery of butadiene from naphtha pyrolysis effluents or refinery butenes where a hydrocarbon stream containing compounds of higher molecular weight than butadiene, including significant amounts of $C_5$ hydrocarbons such as n-pentane, isopentane and 3-methyl butene-1, is conventionally subject to a fractionation or distillation to remove the heavier hydrocarbons prior to extractive distillation. In this situation, misoperation, changes in the feed composition and/or inadequate design of the fractionation zone upstream from extractive distillation can result in significant amounts of $C_5$ hydrocarbons being carried over with the butadiene - containing overhead from fractionation into the extractive distillation zone. In extractive distillation and subsequent butadiene recovery process stages involving flashing and strippin, these $C_5$ hydrocarbons exhibit inconsistent behavior, acting as heavy hydrocarbons in a hydrocarbon environment while having the volatility characteristics of light hydrocarbons in solvent environment. The net effect is that it is very difficult to fractionate mixtures containing both $C_4$ and $C_5$ hydrocarbons in addition to polar solvent and as a result, $C_5$ hydrocarbons tend to accumulate in the process flow subsequent to extractive distillation. The accumulation of these $C_5$ hydrocarbons is also undesirable in that they have a deleterious effect on the rejection of other contaminants from the butadiene product, in particular 1, 2-butadiene and vinyl acetylene, without also incurring excessive solvent loses.

Accordingly, it would be desireable if the extractive distillation process described in U.S. Pat. No. 3,772,158 could be modified in some fashion to eliminate the problems associated with the accumulation of $C_5$ hydrocarbons in the processing steps subsequent to extractive distillation in cases where the hydrocarbon feedstock to extractive distillation is derived from an initial fractionation which unavoidably leaves a minor amount of $C_5$ hydrocarbons in the feedstock. Further, it would be especially advantageous if the accumulation of $C_5$ hydrocarbons could be eliminated or minimized in a way which does not materially increase the cost and complexity of the process.

SUMMARY OF THE INVENTION

A relatively simple and cost effective means has now been found to eliminate the above mentioned problems associated with the accumulation of $C_5$ hydrocarbons in the extractive distillation process of U.S 3,772,158, when said process is employed in conjunction with, and subsequent to, a conventional hydrocarbon fractionation operation to recover butadiene from mixed hydrocarbon streams, such as those obtained in naphtha pyrolysis, which contain significant amounts of $C_5$ hydrocarbons. With this improvement, any accumulation of $C_5$ saturated and unsaturated hydrocarbons, which might otherwise occur due to the presence of a minor amount of $C_5$ hydrocarbons in the fractionated feed to extractive distillation, is readily avoided by condensing out a portion of the compressed butadiene - rich product of low pressure flashing and stripping and passing this condensed product, after solvent removal by water washing, to the initial fractionation zone employed to separate larger quantities of $C_5$ and heavier hydrocarbons from the extractive distillation feed.

This process improvement, which is predicated, in part, on the finding that the $C_5$ hydrocarbons present in the fat solvent from extractive distillation concentrate in the compressor discharge, is quite simple and cost effective because it contemplates the treatment of only a minor process stream relative to the total process flow and involves a minimal expenditure for additional process apparatus. In this latter regard the improved process is especially attractive in that the $C_5$ hydrocarbon separation from the condensed stream is effected in existing equipment i.e. the initial fractionation zone of the conventional process, and only a condenser and water scrubber are required as major additions to existing facilities.

Accordingly the instant invention provides an improved process for recovery of butadiene from a hydrocarbon mixture made up predominantly of $C_4$ hydrocarbons and containing a minor amount of $C_5$ saturated and unsaturated hydrocarbons, said mixture being obtained as overhead product from an initial fractionation step employed to separate larger quantities of $C_5$ and higher hydrocarbons from the $C_4$ hydrocarbon fraction, wherein the hydrocarbon mixture is subject to extractive distillation in the presence of a selective polar solvent and butadiene is separated from the fat solvent bottoms of extractive distillation by sequential flashing and stripping of the fat solvent in low pressure flashing and stripping zones operated at pressures lower than that employed in the extractive distillation to afford vapor products containing predominantly butadiene, a relatively high concentration of $C_5$ hydrocarbons and a minor amount of polar solvent, followed by compression of the combined overhead vapor products of low pressure flashing and stripping and passage of a portion of the compressed vapor product to a second stripping zone operated at a higher pressure for recovery of butadiene as an overhead product with the remainder of the compressed vapor overhead being recycled as reboiled vapor to the extractive distillation step; characterized by the improvement which comprises, a. condensing a portion of the combined vapor overhead product of compression into a liquid stream, b. water washing the condensed liquid stream obtained in step a) to remove polar solvent therefrom leaving a condensed liquid product containing butadiene and a relatively high concentration of $C_5$ saturated and unsaturated hydrocarbons which is substantially free of polar solvent, c. returning the condensed liquid product from step (b) substantially free of polar solvent to the initial fractionation step employed to separate larger quantities of $C_5$ and higher hydrocarbons from the $C_4$ hydrocarbon fraction, whereby $C_5$ saturated and unsaturated hydrocarbons contained in the condensed liquid are substantially removed from the hydrocarbon mixture passed to extractive distillation.

THE DRAWING

The invention will be described in greater detail with reference to the attached FIGURE which depicts a schematic flow diagram of a preferred embodiment of the process according to the invention employing aqueous acetonitrile as the extractive distillation solvent.

DESCRIPTION OF THE PREFERRED EMBODIMENTS

The improvement according to the invention, in its broadest sense, has application in any conventional process arrangement where a mixed hydrocarbon stream containing $C_5$ saturates and unsaturates, in addition to butadiene and other $C_4$ saturates and unsaturates, is first subject to fractionation or distillation to remove a substantial portion of the $C_5$ and heavier hydrocarbons prior to butadiene recovery according to the process of U.S. Pat. No. 3,772,158. Mixed hydrocarbon feedstocks which are conventionally subject to fractionation to remove $C_5$ and heavier hydrocarbon prior to butadiene recovery include mixed refinery butene streams which have previously been subject to catalytic dehydrogenation and naphtha cracking or pyrolysis effluents. The preferred hydrocarbon source in this regard is the butadiene - containing by-product stream which is obtained when naphtha and other petroleum hydrocarbons are cracked or pyrolyzed to produce ethylene.

Depending on the petroleum hydrocarbon feedstock selected e.g., light hydrocarbons such as ethane or propane and light or full-range naphthas, and the severity of the cracking conditions, up to about 20% of the hydrocarbon charge to conventional pyrolysis operations may be converted to by-product butadiene. This by-product butadiene is typically obtained as a crude cracked fraction from pyrolysis which also contains a variety of other $C_4$ hydrocarbons - e.g., isobutane, n-butane, isobutene, 2-butenes, ethylacetylene and the like - as well as $C_5$ and heavier saturated and unsaturated hydrocarbons up to the gasoline boiling range. In conventional practice, the butadiene by-product of cracking is eventually isolated as a crude fraction made up substantially of $C_4$ hydrocarbons by a variety of processing operations which include a final fractionation or debutanization step wherein the $C_4$ hydrocarbons are distilled overhead from any remaining heavy hydrocarbons i.e. $C_5$ and above. This final fractionation step, which is incorporated into the improved extractive distillation process of the invention, is wholly conventional in design and operation; typically involving a thermal distillation in one or more fractionation columns which may be packed or unpacked. While normal operation of this fractionation zone generally affords substantially complete removal of the $C_5$ saturated and unsaturated hydrocarbons from the $C_4$ fraction taken overhead and passed to extractive distillation, there are occassions when minor amounts of $C_5$ hydrocarbons e.g., up to 0.5% by weight, are carried over with the $C_4$ fraction due to misoperation and/or inadequate design of the fractionation column. In the absence of the improvement according to the invention, these minor amounts of $C_5$ hydrocarbons have a deleterious effect on the butadiene recovery because they accumulate in downstream processing steps from extractive distillation and interfere with the rejection of other contaminants from the butadiene. For optimum results with the improvement according to the invention, it is preferred that the quantities of $C_5$ hydrocarbons carried over from fractionation into the extractive distillation feed be no greater than 0.02% by weight of the hydrocarbon feed to extractive distillation. The $C_5$ hydrocarbons present in minor amounts in the $C_4$ hydrocarbon feed to extractive distillation generally include both saturates and unsaturates with n-pentane, isopentane and 3-methyl butene-1being the most predominant.

As pointed out previously, the improvement according to the instant invention finds application when the butadiene recovery process of U.S. Pat. No. 3,772,158 is employed in conjunction with conventional fractionation as described above, to recover butadiene from a $C_4$ hydrocarbon stream containing minor amounts of $C_5$ saturated and unsaturated hydrocarbons. Accordingly, the extractive distillation procedure and subsequent processing steps to recover butadiene from the fat solvent bottoms product as described from the process of U.S. Pat. No. 3,772,158 to Sarno are herewith incorporated by reference. In basic terms, the process of U.S. Pat. No. 3,772,158 provides for the separation of butadiene from mixtures of $C_4$ saturates and unsaturates by (a) introducing the butadiene - containing hydrocarbon mixture into an extractive distillation zone wherein it is distilled in the presence of a selective polar solvent, preferably acetonitrile, whereby substantially all of the olefins and paraffins are recovered as the overhead vapor product from said zone and substantially all of the butadiene is recovered together with the polar solvent as the "fat solvent" bottoms product from said zone; (b) introducing said fat solvent to a flash zone operated at a pressure lower than that of the extractive distillation zone wherein a major portion of the butadiene is vaporized thereby forming a first vapor phase and a partially depleted fat solvent; (c) transferring the partially depleted fat solvent from the bottom of the flash zone to a first stripping zone operated at a pressure lower than that of the extractive distillation zone wherein the remaining butadiene is stripped from the fat solvent thereby forming a second butadiene-rich vapor phase; (d) combining the first vapor phase with the second vapor phase; (e) compressing the combined vapor phases to a pressure higher than that of the extractive distillation zone; (f) returning a portion of the compressed vapor to the bottom of the extractive distillation zone; and, (g) introducing the remaining portion of the compressed vapor to a second stripping zone wherein butadiene is recovered as an overhead product.

In conventional operation of the process described in U.S. Pat. No. 3,772,158, the bulk of the polar solvent is recovered as lean solvent, substantially free of hydrocarbons, at the bottom of the first stripping zone and recycled directly to extractive distillation after heat exchange with recirculated bottoms product from the second stripping zone. When more volatile polar solvents such as acetonitrile are employed, a minor portion of the solvent will also be taken overhead with the olefins and paraffins (butanes and butylenes) in the extractive distillation zone. In these cases, conventional application of the process preferably includes a solvent recovery system wherein the solvent-containing hydrocarbon overhead from extractive distillation is passed to a washing zone where essentially all of the polar solvent is recovered by water washing. This water washing zone is typically comprised of a vertical contacting column equipped with appropriate packing e.g., perforated trays, etc., wherein the water is passed in countercurrent contact with the overhead from extractive distillation and absorbed solvent and water are recovered as a washer bottoms product with the unabsorbed hydrocarbons being taken as washer overhead. The polar solvent contained in the bottoms is then concentrated for recycle to the extractive distillation zone by distillation in a solvent recovery zone. This solvent recovery zone is typically a conventional distillation tower in which the mixed polar solvent-water feed is introduced at an intermediate height and lean polar solvent and essentially pure water are removed as overhead and bottoms products, respectively. To insure the quality of the circulating polar solvent in the extractive distillation and butadiene stripping zones, a small bleed stream of the circulating solvent from the bottom of the first stripping zone is also passed through this solvent recovery system (water washing and solvent recovery zones). In this manner, the build up of heavy hydrocarbons and/or impurities from solvent decomposition is avoided in the circulating solvent.

When the butadiene recovery process described in U.S. Pat. No. 3,772,158 is employed to recover butadiene from a fractionated hydrocarbon feed containing minor amounts of $C_5$ hydrocarbons e.g. up to 0.5% by weight, in addition to $C_4$ saturated and unsaturated hydrocarbons, it has been found that these $C_5$ hydrocarbons tend to reach their highest concentration in the vapor discharge from the compressor employed to compress the combined vapor phases from the flash zone and first stripping zone. Thus, in cases where 0.1 to 0.5% by weight $C_5$ saturated and unsaturated hydrocarbons are present in the feed to extractive distillation, it is possible to encounter $C_5$ hydrocarbon concentrations as high as 15% by weight in the compressed vapor discharge. The balance of this compressed vapor discharge is predominantly butadiene though a minor amount of polar solvent is also generally present. In accordance with the improved process of this invention, any accumulation of $C_5$ hydrocarbons is avoided by (a) withdrawing a porton of the vapor from the compressor discharge containing the high concentration of $C_5$ hydrocarbons relative to that present in the hydrocarbon feed to extractive distillation, (b) condensing this vapor to a liquid stream and (c) water washing the condensed liquid stream to remove polar solvent therefrom, after which (d) the condensed liquid stream substantially free of polar solvent is recycled to the fractionation zone preceding extractive distillation where adequate rejection of the $C_5$ hydrocarbons to the fractionation zone bottoms takes place.

The portion of compressor vapor discharge withdrawn in the improved process of the invention will depend to a certain degree on the quantity of $C_5$ hydrocarbons present in the compressor discharge and the amount of $C_5$ hydrocarbons which can be tolerated in the butadiene recovery system without causing disruption. In most applications stable operation is possible with up to 10% of $C_5$ hydrocarbons by weight in the compressor discharge. Thus a sufficient quantity of compressor discharge vapor must be withdrawn to at at least maintain this level of $C_5$ hydrocarbons in the compressor discharge. Generally, the amount of compressor discharge vapor withdrawn and treated according to the invention will be only a minor portion of the total compressor discharge e.g. less than about 10% by weight. Preferably, the amount of compressor discharge vapor withdrawn is less than about 3% by weight of the total vapor discharge. After separation from the compressor discharge, this vapor stream is passed thorugh a condenser where it is cooled to a temperature below its dew point. This condenser is of conventional design i.e. externally cooled tube and shell heat exchanger, and is supplied with sufficient coolant to reduce the temperature of the vapor stream to a level where it is substantially in the liquid form. Typically, the temperature of the liquid effluent from the condenser will be in the range of 35° to 45° C.

After condensation, the liquid stream containing butadiene, a relatively high concentration of $C_5$ hydrocarbons and a minor amount of polar solvent is passed to a water washing zone where it is contacted with water to absorb and remove any polar solvent contained therein. This water washing zone is typically a vertically oriented, liquid contacting column equipped with appropriate packing, in which the condensed liquid stream, charged to the lower portion of the column, is counter-currently contacted with a water stream introduced into the upper portion of the column. With this conventional washing zone design, a hydrocarbon effluent is obtained at the top of the column which is substantially free of polar solvent while the wash water, containing polar solvent, is recovered as a bottoms product from the column. Condensed liquid to water weight ratios of about 0.2 to 0.4 and 4 to 6 theoretical mixing stages are generally sufficient to obtain substantially complete removal of polar solvent in this washing zone.

Removal of the $C_5$ hydrocarbons from the condensed and water-washed hydrocarbon stream is effected by passing the hydrocarbon effluent from the water washing zone back to the initial fractionation zone, immediately upstream from the extractive distillation zone. In this fractionation zone, the $C_5$ hydrocarbons contained in the condensed and water-washed stream are substantially removed from the feed to extractive distillation as part of the larger quantity of heavy hydrocarbons taken as a bottoms product from that zone. Utilization of the initial fractionation zone as a means to remove $C_5$ hydrocarbons from the condensed and water hydrocarbon stream is of advantage in that the need for separate $C_5$ hydrocarbon removal facilities is avoided and the butadiene contained in the condensed stream is made directly available to extractive distillation. Further, since the quantity of condensed and water washed hydrocarbon recycled to the initial fractionation zone is generally quite small with respect to the total hydrocarbon flow handled by that zone e.g., less than 2% of the total hydrocarbon charge, very little, if any, modification of the fractionation zone design and operation is necessary to accomodate this recycle stream.

Additional advantages are obtained for the improved process of the invention if existing facilities are employed to recover polar solvent from the polar solvent-containing wash water emanating from the washing zone employed to remove polar solvent from the condensed compressor vapor. Accordingly, in a preferred embodiment of the invention, this polar solvent containing wash water is passed to the solvent recovery system of the extractive distillation process where it is combined with the water washed solvent stream and the polar solvent containing aqueous bottoms stream from the counter-current washing of the extractive distillation overhead; and this combined stream is then concentrated for recycle by distillation in the solvent recovery zone. The total flow of solvent-containing wash water from the washing zone according to the invention is quite small relative to the total quantity of aqueous solvent handled by the solvent recovery system, i.e., typically being less than 4% of the total water washed solvent handled by the system. Thus, it is possible to pass this solvent-containing wash water directly to the solvent recovery system with little, if any, modification of the distillation column employed in that system.

Reference will now be made to the attached Figure which represents a schematic flow diagram of a preferred embodiment of the present invention wherein butadiene is recovered from a naphtha pyrolysis effluent by sequential fractionation and extractive distillation employing aqueous acetonitrile. It is to be understood that the Figure is only a schematic representation of the process and does not purport to show the conventional instrumentation and valving present in a typical process.

A hydrocarbon feed comprising the $C_4$ fraction from naphtha pyrolysis typically containing e.g., 45% by weight, of $C_5$ and heavier hydrocarbons, is introduced via line 11 into a conventional fractionation zone or debutanizer, 10, at an intermediate point. This fractionation zone or distillation column typically operates at a bottoms temperature of 100° C and a pressure of 78 psia. From this fractionation zone, a light hydrocarbon stream made up substantially of $C_4$ olefins and paraffins and containing a minor amount e.g. 0.5% by weight, of $C_5$ saturated and unsaturated hydrocarbons is taken overhead by line 12 and passed to an intermediate point in the extractive distillation zone, 20. Substantially all of the $C_5$ and heavier hydrocarbons contained in the hydrocarbon feed to fractionation are removed as a bottoms product by line 13.

Acetonitrile solvent containing approximately 10% by weight water enters at the top portion of the extractive distillation zone 20, via line 21 at a temperature of approximately 45° C. This extractive distillation zone, 20, is typically a vertical column which operates at a top pressure of about 85 psia and a bottoms pressure of about 100 psia. A hydrocarbon stream containing $C_4$ olefins and paraffins and a minor amount of acetonitrile solvent which is substantially free of butadiene, is removed as an overhead product via Line 22 and passed to the water washing zone, 80, of the solvent recovery system. A fat solvent containing essentially butadiene, any acetylenes such as vinyl and ethyl acetylene, a minor amount of $C_5$ hydrocarbons and the aqueous acetonitrile solvent is removed from the base of the extractive distillation column 20 via Line 23. The thermal energy required for the extractive distillation is supplied by the butadiene-rich vapor which is introduced via Line 42 into the bottom of the extractive distillation column 20. In this way, a comparatively low temperature of approximately 85° C is maintained in the bottom of the extractive distillation column 20.

The fat solvent from the bottom of the extractive distillation column 20 is carried via Line 23 to a flash drum 30, operated at a pressure of approximately 40 psia, wherein a major portion of the butadiene and at least some of the $C_5$ hydrocarbons contained in the fat solvent vaporize at the lower pressure. The temperature in the flash drum 30 is approximately 70° C. The butadiene-rich vapor which collects in the top of the flash drum 30 is carried by Lines 31 and 32 to the suction of compressor 50. The fat solvent partially depleted of butadiene collects in the bottom of the flash drum 30 and is carried by Line 33 to the upper portion of the first stripping column 40.

In the first stripping column 40 heat is added via a reboiler 46 to strip the remaining butadiene from the fat solvent. A butadiene-rich vapor containing the remainder of the $C_5$ hydrocarbons is recovered as an overhead product and is carried via Line 41 to the suction of compressor 50 where it is combined with the butadiene-rich vapor obtained from the flash drum 30 in line 32. Lean solvent stripped of essentially all of the butadiene is recovered as a bottoms product via Line 42 and recycled back to the extractive distillation zone, 20, via line 21, after heat exchange with recirculated bottoms from the second stripping zone, 60.

The operating pressure of the first stripping column 40 is approximately 40 psia which results in a comparatively low bottoms temperature of 115° C. The low temperature enhances the difference in relative volatility between butadiene and vinyl acetylene with the result that the acetylene content of the final butadiene product is maintained at a relatively low level by withdrawing a solvent-rich stream rich in acetylenes via Line 43 from an intermediate point the first stripping column 40. From this stream the acetylenes can be removed in a side draw stripper (not shown in the drawing) or by other appropriate means.

The butadiene-rich vapor streams from the flash drum 30 and the overhead from the first stripping column 40 are combined and compressed by means of a compressor 50 to a pressure of approximately 115 psia. It is at this point in the process flow that the $C_5$ hydrocarbons tend to reach their highest concentration, comprising from about 2 to about 15% by weight of the compressed vapor stream. A minor amount of acetonitrile solvent e.g. 8% by weight, is also present in this compressed vapor stream. According to the invention, this compressed vapor stream discharged from the compressor, 50, via line 51 is divided into three portions. The bulk of the compressed vapor stream is split between lines 52 and 53 for recycle to the bottom of the extractive distillation column 20, and transfer to the second stripping column, 60, respectively.

The remainder of the compressed vapor discharge, typically less than 10% of the total discharge, is passed via line 54 to the condenser, 55, where it is cooled to a temperature below its bubble point. The cooled liquid effluent from the condenser is passed by line 56, at a temperature of about 40° C to the bottom of the condensed liquid, water washing zone, 70, where it is contacted with wash water introduced via line 71 into the upper portion of the washing zone. Any acetonitrile contained in the condensed liquid stream is absorbed in this water-washing zone and removed as an aqueous acetonitrile bottoms product via line 72 for transfer to the distillation zone, 90, of the solvent recovery system. The water-washed hydrocarbon stream, substantially free of acetonitrile, is taken overhead from the washing zone, 70, by line 73 and transfered back via the hydrocarbon feed line 11, to the fractionation zone, 10, where the $C_5$ hydrocarbons contained in the condensed and water washed liquid stream are removed as a fractionation zone bottoms product along with other heavy hydrocarbons contained in the hydrocarbon feed.

Butadiene is recovered as overhead product of the second stripping zone 60, via line 61. This second stripping column, 60, is operated at an overhead pressure of approximately 85 psia to facilitate the condensation of the overhead butadiene vapors with normal cooling water. Lean solvent split off the lean solvent recycle is injected via Line 62 near the top of the column to facilitate the separation of acetylenic materials from the butadiene product. A solvent-rich bottoms product is recycled via Line 63 to the top of the first stripping column 40 wherein the butadiene and acetylenic materials are separated from the solvent. Thermal energy for the stripping operation is provided by recirculating a portion of the stripping zone bottoms product via line 64 through a bottoms exchanger 65 wherein heat is exchanged with hot lean solvent from the bottoms of the first stripping column 40. The maximum temperature attained in the bottoms of the second stripping column 60 is approximately 80° C.

In this preferred embodiment shown, acetonitrile solvent is recovered from the hydrocarbon overhead of extractive distillation in line 22 and the condensed liquid, water-washed bottoms product in line 72 with a solvent recovery system comprising a water washing zone, 80, and a distillation zone 90. It is also preferred that a portion of the lean solvent bottoms product from the first stripping zone, 40, which is recycled to the extractive distillation zone 20, via line 42, be circulated through the solvent recovery system to maintain the quality of the recycled solvent in the system. This is accomplished by splitting off a minor portion of the recycle stream typically less than 1.0% of the total stream, via line 81 and passing it to the bottom portion of the solvent recovery water washing zone 80. Also introduced into the bottom of this water washing zone, 80, is the hydrocarbon overhead stream in line 22. These two streams may be introduced separately, as shown, or as a combined stream. In the water washing zone, 80, the solvent containing streams are contacted with wash water, introduced at the top of the zone via line 82 to afford a substantially solvent free hydrocarbon overhead which is passed by line 83 to further service and an aqueous acetonitrile bottoms product which is transfered via lines 84 and 91 to the distillation zone 90. Prior to passage to the distillation zone, 91, the acetonitrile-containing bottom product in line 72 from the condensed liquid washing zone, 70, is combined with the aqueous acetonitrile bottoms product in line 91. This combined stream is subject to thermal distillation in the distillation zone 90, to yield a lean solvent overhead, 92, of near-azeotropic composition and a substantially solvent-free aqueous bottoms product in line 93 which is employed as the wash water charge to the washing zone 80 after removal of a small side stream via line 94 to avoid the buildup of undesirable impurities. A portion of the lean solvent overhead from the distillation zone, 90, is recirculated to the top of that zone via line 95 as reflux and the remainder is transfered by line 96 back to the solvent feed line, 21, for extractive distillation. If desired, additional make up solvent can be added to the system via line 97.

What is claimed is:

1. In the process for recovery of butadiene from a hydrocarbon mixture made up predominantly of $C_4$ hydrocarbons and containing a minor amount of $C_5$ saturated and unsaturated hydrocarbons, said mixture being obtained as overhead product from an initial fractionation step employed to separate larger quantities of $C_5$ and higher hydrocarbons from the $C_4$ hydrocarbon fraction, wherein the hydrocarbon mixture is subject to extractive distillation in the presence of a selective polar solvent and butadiene is separated from the fat solvent bottoms of extractive distillation by sequential flashing and stripping of the fat solvent in low pressure flashing and stripping zones operated at pressures lower than that employed in the extractive distillation to afford vapor products containing predominantly butadiene, a relatively high concentration of $C_5$ hydrocarbons and a minor amount of polar solvent, followed by compression of the combined overhead vapor products of low pressure flashing and stripping and passage of a portion of the compressed vapor product to a second stripping zone operated at a higher pressure for recovery of butadiene as an overhead product with the remainder of the compressed vapor overhead being recycled as reboiled vapor to the extractive distillation step; the improvement which comprises, a. condensing a portion of the combined vapor overhead product of compression into a liquid stream,
b. water washing the condensed liquid stream obtained in step (a) to remove polar solvent therefrom leaving a liquid product containing butadiene and a relatively high concentration of $C_5$ saturated and unsaturated hydrocarbons which is substantially free of polar solvent,
c. returning the condensed liquid product from step (b) substantially free of polar solvent to the initial fractionation step employed to separate larger quantities of $C_5$ and higher hydrocarbons from the $C_4$ hydrocarbon fraction whereby $C_5$ saturated and unsaturated hydrocarbons contained in the condensed liquid are substantially removed from the hydrocarbon mixture passed to extractive distillation.

2. The process according to claim 1 wherein the hydrocarbon mixture is obtained as overhead product from an initial fractionation of a butadiene-containing by-product stream from petroleum hydrocarbon pyrolysis.

3. The process according to claim 2, wherein the hydrocarbon mixture contains up to about 0.5% by weight $C_5$ hydrocarbons.

4. The process according to claim 1, wherein the polar solvent is recovered as lean solvent, substantially free of hydrocarbons at the bottom of the low pressure stripping zone and the lean solvent is recycled to extractive distillation.

5. The process according to claim 4, wherein further solvent recovery is facilitated by passing the overhead product of extractive distillation and a minor portion of the lean solvent recovered at the bottom of the low pressure stripping zone to a solvent recovery system comprising a water washing zone and a distillation zone in which solvent is recovered in admixture with water as a washing zone bottoms product and the washing zone bottoms product is passed to the distillation zone wherein the polar solvent contained therein is concentrated for recycle to extractive distillation, said concentrated polar solvent being removed as an overhead product of distillation and recycled to extractive distillation.

6. The process according to claim 5, wherein the polar solvent removed by water washing of the condensed liquid product in step (b) is recovered by passing the water washed solvent to the distillation zone of the solvent recovery system.

7. The process according to claim 1 wherein the polar solvent is acetonitrile.

8. The process according to claim 6, wherein the polar solvent is acetonitrile.

* * * * *